(12) United States Patent
Landowski

(10) Patent No.: US 8,714,056 B2
(45) Date of Patent: May 6, 2014

(54) TORQUE LIMITING MECHANISM WITH LOCK BUSHING

(75) Inventor: Steve Landowski, Paddock Lake, WI (US)

(73) Assignee: Greatbatch Ltd., Clarence, NY (US)

( * ) Notice: Subject to any disclaimer, the term of this patent is extended or adjusted under 35 U.S.C. 154(b) by 263 days.

(21) Appl. No.: 13/224,659

(22) Filed: Sep. 2, 2011

(65) Prior Publication Data

US 2012/0055296 A1 Mar. 8, 2012

Related U.S. Application Data

(60) Provisional application No. 61/379,938, filed on Sep. 3, 2010.

(51) Int. Cl.
*B25B 23/143* (2006.01)

(52) U.S. Cl.
USPC .......................................................... 81/474

(58) Field of Classification Search
USPC ................................ 81/467, 473–476; 464/36
See application file for complete search history.

(56) References Cited

U.S. PATENT DOCUMENTS

| | | | |
|---|---|---|---|
| 3,702,546 A | 11/1972 | Schnepel | |
| 4,488,604 A * | 12/1984 | Whitehouse | ................. 81/469 |
| D278,593 S | 4/1985 | MacGregor | |
| D304,543 S | 11/1989 | Somers et al. | |
| 5,069,091 A | 12/1991 | Bramsiepe et al. | |
| D323,449 S | 1/1992 | Corona et al. | |
| 5,228,363 A | 7/1993 | Corona et al. | |
| 5,239,875 A | 8/1993 | Stasiek et al. | |
| D371,499 S | 7/1996 | Gomas | |
| D375,669 S | 11/1996 | Shiao | |
| D378,729 S | 4/1997 | Chang | |
| D384,565 S | 10/1997 | Lin | |
| 5,848,680 A | 12/1998 | Rinner | |
| D421,888 S | 3/2000 | Thompson et al. | |
| 6,047,617 A | 4/2000 | Chen | |
| D431,989 S | 10/2000 | Lai | |
| 6,132,435 A * | 10/2000 | Young | ................. 606/104 |
| D435,773 S | 1/2001 | Lin | |
| D435,774 S | 1/2001 | Chen | |
| D449,505 S | 10/2001 | Glass et al. | |
| 6,370,988 B1 | 4/2002 | Thompson et al. | |
| D461,389 S | 8/2002 | Hsiao | |
| D476,875 S | 7/2003 | Chen | |
| D481,612 S | 11/2003 | Tsai | |
| 6,701,814 B2 | 3/2004 | Purkapile | |
| D515,388 S | 2/2006 | Howard | |
| D529,366 S | 10/2006 | Wang | |
| 7,127,955 B2 | 10/2006 | Bondhus et al. | |
| 7,137,320 B2 | 11/2006 | Tuan-Mu | |
| 7,168,342 B2 | 1/2007 | Gao et al. | |
| D536,234 S | 2/2007 | Lin | |

(Continued)

OTHER PUBLICATIONS

European search, Feb. 14, 2013, 11180000.9.

*Primary Examiner* — Hadi Shakeri
(74) *Attorney, Agent, or Firm* — Michael F. Scalise

(57) ABSTRACT

A torque limiting mechanism used for securing fasteners is described. The torque limiting mechanism consists of a shaft, a torque gear having a plurality of ball bearings, a threshold bearing and a variable force applying subassembly. The torque limiting mechanism further consisting of a lock bushing and retaining ring placed circumferentially around the proximal end of the shaft. The lock bushing and retaining ring reduce structural misalignments and increase the accuracy of the device.

23 Claims, 4 Drawing Sheets

(56) References Cited

U.S. PATENT DOCUMENTS

| | | |
|---|---|---|
| D550,531 S | 9/2007 | Yeh |
| 7,275,466 B2 | 10/2007 | Cluthe |
| 7,290,465 B2 | 11/2007 | Gao et al. |
| 7,334,509 B1 | 2/2008 | Gao |
| 7,421,772 B2 | 9/2008 | Gao et al. |
| 7,467,576 B2 | 12/2008 | Gao |
| 7,503,443 B1 * | 3/2009 | Dobras .................. 81/474 |
| D600,991 S | 9/2009 | Lai |
| 7,597,031 B2 | 10/2009 | Chiang |
| 7,600,451 B2 | 10/2009 | Lechot et al. |
| 7,647,852 B1 | 1/2010 | Rinner |
| 7,650,821 B2 * | 1/2010 | Gauthier et al. ................ 81/473 |
| 2007/0107563 A1 | 5/2007 | Hu |
| 2008/0087146 A1 | 4/2008 | Gao |
| 2009/0326545 A1 | 12/2009 | Schaffhausen |
| 2010/0005931 A1 | 1/2010 | Lai |
| 2010/0018366 A1 | 1/2010 | Hu |
| 2010/0204703 A1 | 8/2010 | Gao |

* cited by examiner

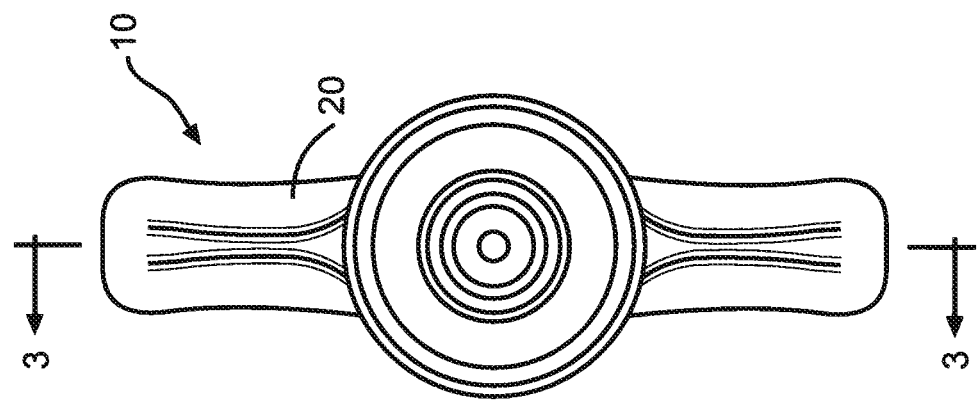
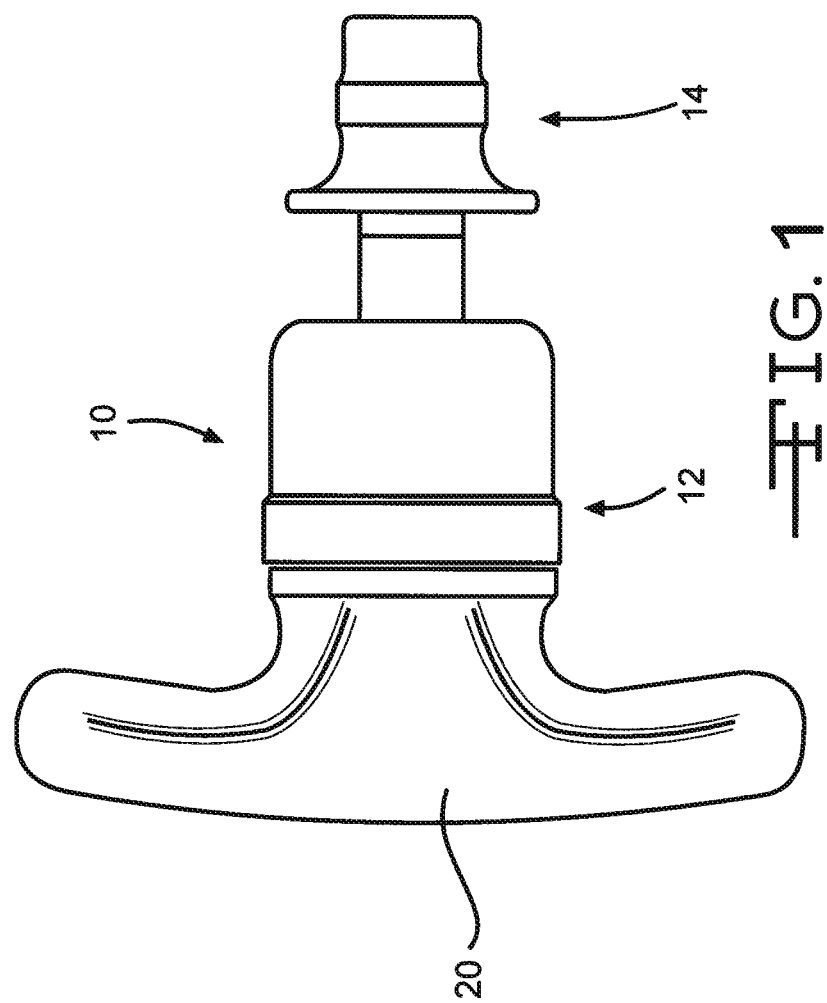

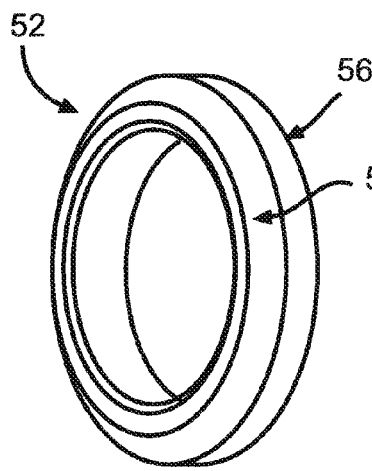
FIG. 5
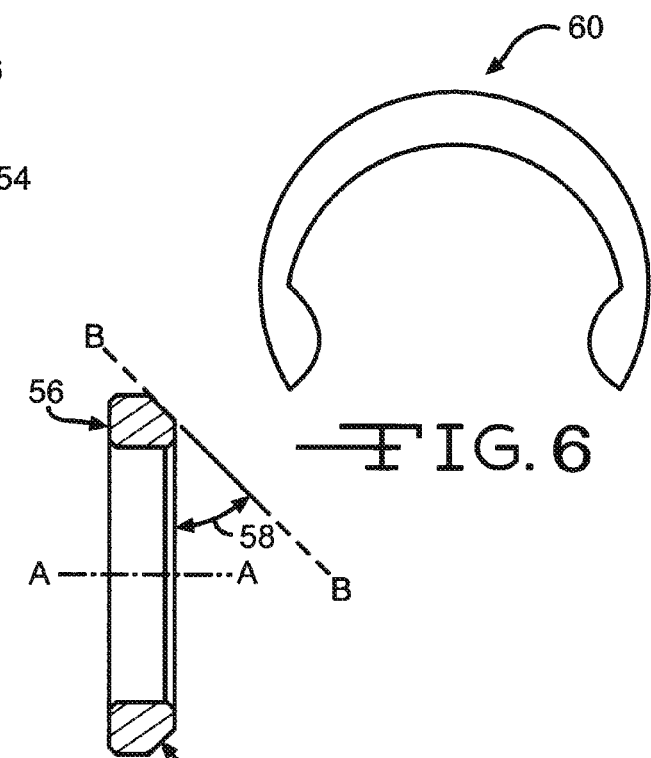
FIG. 5A
FIG. 6
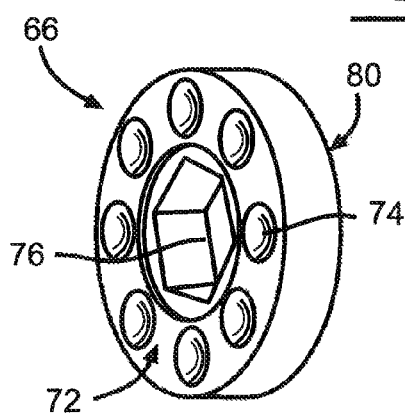
FIG. 7
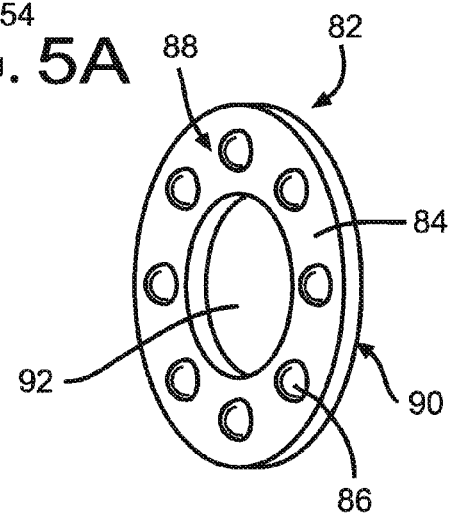
FIG. 8

TORQUE LIMITING MECHANISM WITH LOCK BUSHING

CROSS REFERENCE TO RELATED APPLICATIONS

This application claims priority to U.S. provisional application Ser. No. 61/379,938, filed on Sep. 3, 2010.

FIELD OF THE INVENTION

This invention relates to surgical tools for aiding in installing orthopedic prostheses, and more specifically, to an improved torque limiter device for installing orthopedic implants.

BACKGROUND OF THE INVENTION

Torque limiting devices have been utilized in various medical applications. For example, torque limiter devices have been used to fasten nuts and bolts that are utilized to secure surgical implements such as orthopedic implants. As such, it is important that these devices enable the user to apply a consistent and exacting amount of torque. The delivery of an exact amount of torque is critical in securing an implant or other surgical implement in the correct position without causing damage to the implant and the patient.

Prior art torque limiting devices are typically constructed with torque gear teeth that tend to bind against the shaft within the torque limiter device. These prior art devices are typically designed such that as the torque gear is rotated within the device, the gear tends to rotate at a slight angle, away from its horizontal position relative to the longitudinal shaft. This misalignment of the torque gear with respect to the longitudinal shaft within these prior torque limiters creates a frictional interference within the device. Such misalignments results in inaccurate torque outputs as well as increased mechanical wear of the device.

In addition, these prior art torque limiter devices are typically constructed with a plurality of intricate and complex components that are intended to fit and work precisely together. However, the complexity and increased number of components generally result in tolerance stack up and other structural misalignments. The cumulative effects of these misalignments further contribute to the inaccuracy of the device as well as to the increased mechanical wear of the device. These inaccuracies are particularly prevalent at low torque ranges, especially when applying a torque at less than 20 inch-lbs. Moreover, it has been known that the act of pushing down on the handle of these prior art devices during their normal standard use could result in the application of an additional 0.5 to 2 inch-lbs. of torque, particularly at these low torque ranges. Since it is critical that the precise amount of torque be applied during surgical procedures, over torquing a fastener could damage the surgical implant and may result in undesirable patient outcomes.

The torque limiter device of the present invention addresses these shortcomings of the prior art. The present invention provides a more accurate device that is designed with a less complicated torque limiting mechanism. The torque limiting mechanism of the present invention minimizes these structural misalignments with the incorporation of a lock bushing and retaining ring within the device. The lock bushing and retaining ring ensure that the shaft of the mechanism rotates true and unobstructed. The simplified novel design further corrects the misalignment issues of the prior art and thus improves the accuracy with which torque is applied. Therefore, the features and structural design of the torque limiting device of the present invention ensure that the proper amount of torque is delivered while securing an implant fastener, thus minimizing possible structural damage to the implant and ensuring patient safety.

SUMMARY OF THE INVENTION

The present invention provides a torque limiter device that is designed to secure a threaded fastener such as a bolt, screw or nut to a specified torque value. Fasteners are often used in surgical applications such as to secure an orthopedic implant or other device within the body. The present invention can be used as a hand held instrument or may be utilized as a power driven device. The torque limiting mechanism of the present invention primarily comprises a housing, an elongated body with a plurality of springs or washers, a threshold bearing, a torque gear, and a series of ball bearings. These components are arranged circumferentially about the elongated body or shaft such that the washers or springs compress the threshold bearing against the torque gear. The torque gear, which is connected to the elongated body or shaft, compresses against the ball bearings, which in turn compress against an internal surface of the housing. The mechanism further comprises a lock bushing and retaining ring that reside at the proximal end of the elongated body. The lock bushing and retaining ring ensure proper alignment and minimize lateral movement of the components within the device, particularly the elongated shaft with respect to the series of ball bearings and the torque gear. Such improvements in alignment of the elongated shaft with respect to the torque gear afforded by the lock bushing and retaining ring contribute to the increased accuracy of the present invention.

Furthermore, the structural design of the torque limiter device of the present invention comprises fewer components than those of typical prior art devices. As previously mentioned, the torque gear of the present invention lacks the gear teeth, which tend to bind against the shaft of the device. Therefore, elimination of these gear teeth reduces this binding problem. Furthermore, the overall reduction in the number of components reduces the complexity of the instrument and minimizes stack up and alignment, issues that plague previous devices.

The housing of the device is also designed with a series of cavities that are dimensioned such that the components of the device seat properly therewithin. Specifically, this feature of the present invention contributes to the proper alignment of the components within the device, particularly that of the elongated body and ball bearings as they rotate in applying torque.

The improved structural alignments afforded by the features of the present invention directly translate into increased accuracy and precision of the instrument. Specifically, the design features of the present invention reduce the tendency of the elongated shaft to bind with the torque gear. In addition, the features of the present invention reduce tolerance and component stack up issues therewithin. The features of the device of the present invention, therefore, provide a torque limiter device with improved accuracy and performance as compared to prior torque limiting devices. Such improvements in accuracy of the instrument minimize the possibility of implant damage and resulting patient harm.

BRIEF DESCRIPTION OF THE FIGURES

FIG. 1 illustrates a side view of the torque limiter device of the present invention.

FIG. 2 shows an end view of the present torque limiter device.

FIG. 5 illustrates a perspective view of an embodiment of the lock bushing.

FIG. 5A illustrates a cross-sectional view of the lock bushing.

FIG. 6 shows a side view of an embodiment of the retaining ring.

FIG. 7 shows a perspective view of an embodiment of the torque gear.

FIG. 8 illustrates a perspective view of an embodiment of the thrust bearing.

DETAILED DESCRIPTION OF THE INVENTION

Figure 3:
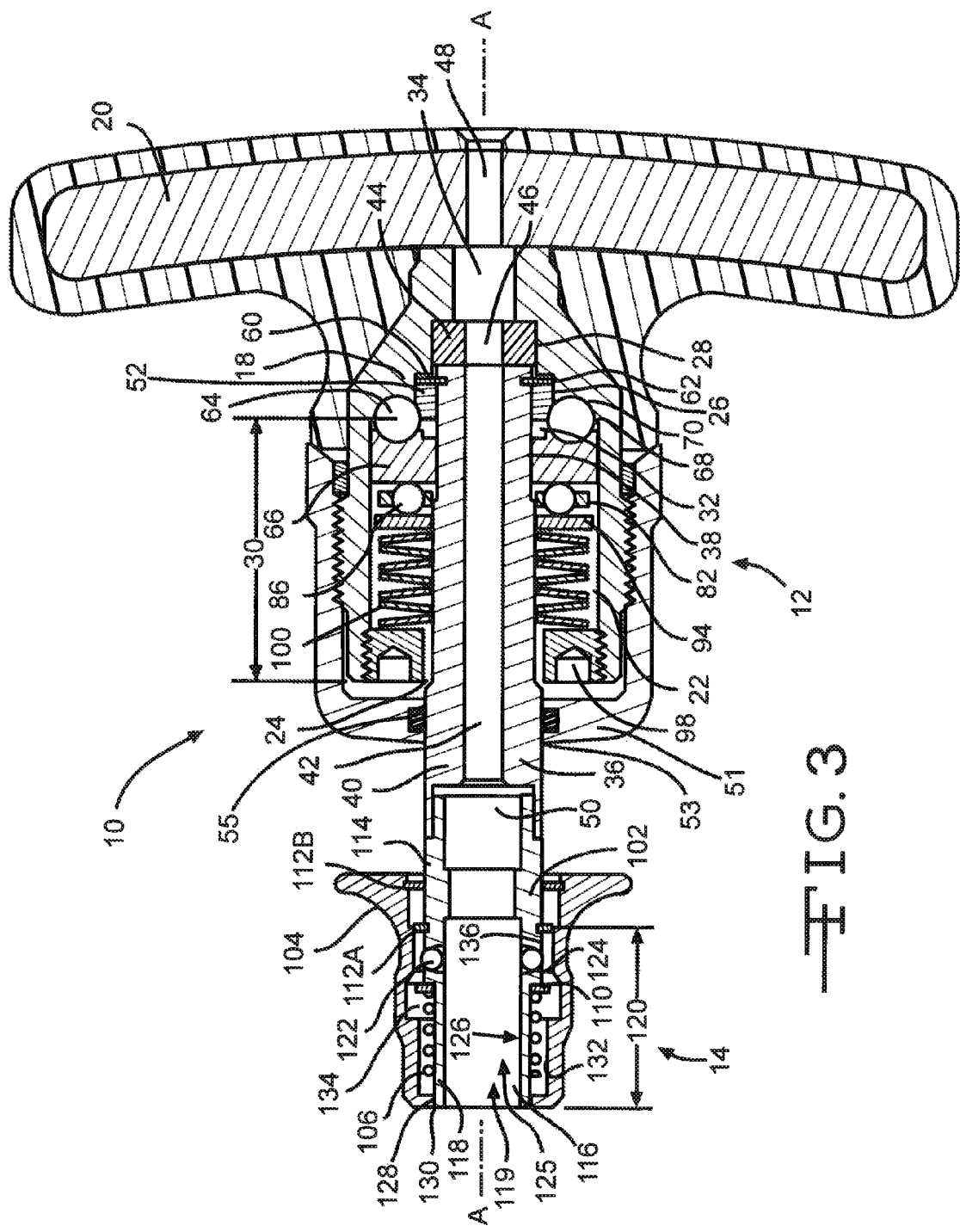
FIG. 3 illustrates a cross-sectional view of the torque limiter device.

Referring now to the figures, FIGS. 1-5, 5A and 6-8 illustrate embodiments of a torque limiter device assembly 10 of the present invention and associated components. The device assembly 10 comprises a torque limiter device 12 and an adapter 14 connected therebetween. The torque limiter device 12, having a distal end portion spaced apart from a proximal end portion, further comprises a torque limiting mechanism 16 therewithin. The torque limiting mechanism 16 resides within a housing 18 of the device 12. A handle portion 20 is fluidly connected to the proximal end of the housing 18 of the device 12.

As shown in FIG. 3, the housing portion 18 has a first cavity 22 with a first cavity opening 24 that extends from the distal end of the housing 18. The first cavity 22 transitions into a second cavity 26, and the second cavity 26 further transitions into a third cavity 28. The second cavity 26 is proximal of the first cavity 22 and the third cavity 28 is proximal of the second cavity 26. In a preferred embodiment, the opening 24 of the first cavity 22 has a curved cross-section. More preferably, the opening 24 of the first cavity 22 has a round cross-section. However, it is contemplated that the opening 24 of the first cavity 22 as well as the openings of the other cavities within the housing 18 may be of a number of cross-sectional shapes not limited to circular, rectangular, triangle, hexagonal and the like. These cavities 22, 26, 28 of the housing 18 are dimensioned such that the components of the torque limiting mechanism 16 reside therewithin. It is preferred that the first cavity 22 is dimensioned such that its diameter is greater than the diameter of the second cavity 26 and the second cavity 26 is dimensioned such that its diameter is greater than the third cavity 28. In a preferred embodiment, the first cavity 22 has a diameter ranging from about 1.0 cm to about 5.0 cm. The first cavity 22 further having a first cavity depth 30 ranging from about 1 cm to about 5 cm.

The second cavity 26 transitions proximally from the first cavity 22 in a stepwise manner. The second cavity 26 has a second cavity opening 32 that extends from the proximal end of the first cavity 22. In a preferred embodiment, the second cavity 26 has a diameter from about 1 cm to about 4 cm and a second cavity depth that ranges from about 1 cm to about 5 cm. The third cavity 28 transitions proximally from the second cavity 26 in a stepwise manner. The third cavity 28 preferably has a diameter from about 1 cm to about 3 cm and a third cavity depth that ranges from about 1 cm to about 5 cm. A housing throughbore 34 extends from the proximal end of the third cavity 28 through the proximal end of the housing 18. It is preferred that the housing throughbore 34 has a diameter that is less than the diameter of the third cavity 26.

An elongated body or shaft 36, having a proximal end portion 38 spaced apart from a distal end portion 40, is positioned within the housing 18 of the device 12. The shaft 36 further has an elongated throughbore 42 extending therethrough. In a preferred embodiment, the shaft 36 is centered in the housing 18 such that the shaft 36 is parallel to a longitudinal axis A-A extending from the proximal end of the device 12 to the distal end thereof.

The proximal end portion 38 of the shaft 36 resides within the housing 18, specifically within the opening of the third cavity 28 within the housing 18. A bearing 44 having a bearing throughbore 46 is preferably positioned proximal of the shaft 36. The bearing throughbore 46 and shaft throughbore 42 are positioned such that they are co-axial with the housing throughbore 34.

Furthermore, the bearing throughbore 46 is positioned co-axial to a cannulation 48 which extends through the handle portion 20. The cannulation 48 preferably extends from the proximal end of the housing throughbore 34 to the proximal end of the handle 20. The cannulation 48 is designed to allow for a thorough cleaning within the device 12. In a preferred embodiment, the cannulation 48 provides an opening for the introduction and subsequent draining of cleaning solutions therewithin. Furthermore, the cannulation 48 allows for the insertion of a catheter, a needle, a sheath, or the like within the device 12, if so desired. In a preferred embodiment, the cannulation 48 has a diameter ranging from about 0.5 cm to about 5 cm.

The distal end portion 40 of the shaft 36 may comprise a socket opening 50. The socket opening 50 provides an opening that is designed to mate with a nut, bolt, screw or another shaft. In a preferred embodiment, the socket opening 50 may have a cross-sectional shape comprising a rectangle, a square, a triangle, an oval, a hexagonal or the like.

Figure 4:
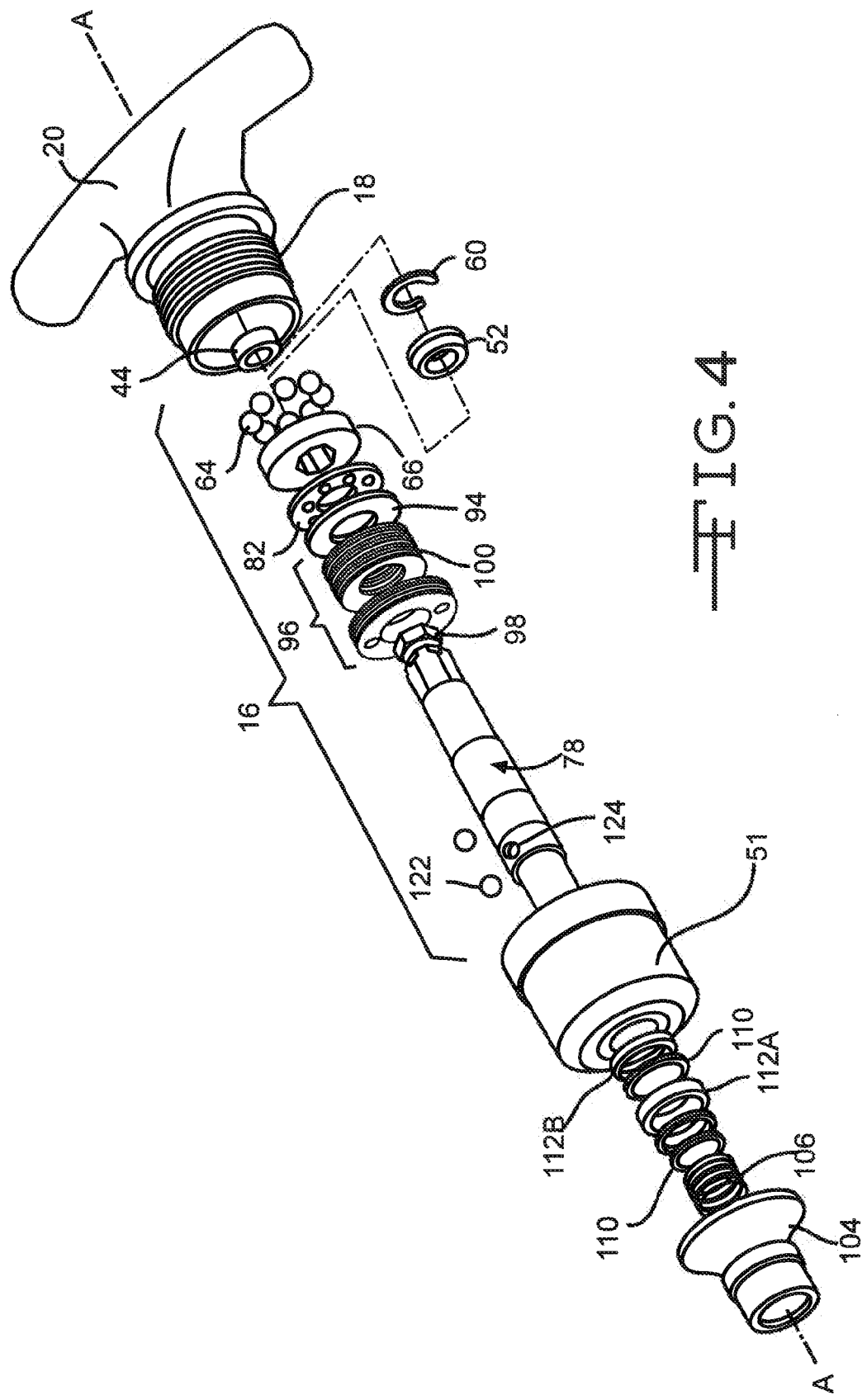
FIG. 4 shows an exploded view of the components comprising the torque limiter device of the present invention.

In a preferred embodiment, a lock bushing 52 is positioned circumferentially around the outer diameter of the proximal end portion 38 of the shaft 36, as illustrated in FIG. 3. The lock bushing 52, as shown in FIGS. 4, 5 and 5A, has a distal surface 54 that is spaced apart from a proximal surface 56. The distal surface 54 is further designed such that it is angled with respect to longitudinal axis A-A. In a preferred embodiment, the distal surface 54 of the lock bushing 52 slopes downwardly at a lock bearing angle 58 ranging from about 35° to about 50° with respect to longitudinal axis A-A. The lock bearing angle 58 is herein defined as the angle between tangent line B-B and longitudinal axis A-A.

The proximal surface 56 of the lock bushing 52 preferably is about perpendicular with respect to longitudinal axis A-A. In a preferred embodiment, the lock bushing is positioned within the second cavity 26 such that its outer diameter approximates the diameter of the second cavity 26. Furthermore, the lock bushing 52 is positioned such that its proximal surface 56 contacts a first retaining ring 60 and its distal surface 54 faces toward the distal end of the device 12.

The first retaining ring 60 (FIG. 6) is positioned circumferentially around the proximal end portion 38 of the shaft 36 proximal of the lock bushing 52. The retaining ring 60 is preferably positioned such that it abuts a proximal wall surface 62 of the second cavity 26. Furthermore, the first retaining ring 60 has an outer diameter that approximates the inner diameter of the second cavity 26. The first retaining ring 60 in concert with the lock bushing 52 provide structural stability and improved alignment of the elongated body or shaft 36. The first retaining ring 60 and lock bushing 52 allow for the shaft 36 to freely rotate within the Second cavity 26. At the same time, they prevent lateral movement of the shaft 36 such that the shaft 36 does not become skewed or cocked from the central longitudinal axis A-A. In addition, the first retaining ring 60 serves as a "back stop" to prevent the lock bushing 52 from travelling proximally down the shaft 36.

A plurality of ball bearings 64 are positioned circumferentially around the shaft 36. In a preferred embodiment, eight ball bearings 64 are positioned about the shaft 36. However, it is contemplated that more or less than eight ball bearings 64 may be used. As shown in FIG. 3, each of the ball bearings 64 resides between a torque gear 66, positioned distal of the ball bearings 64, and a proximal wall surface 68 of the first cavity 22 and the distal surface 54 of the lock bushing 52. These three points of ball contact position each of the series of balls 64 such that migration and lateral movement of the ball bearings 64 is minimized.

Furthermore, each of the ball bearings 64 is nested in a recess 70 provided in the proximal surface 68 of the first cavity 22 of the housing 18. The recess 70 provides a seat within which the ball bearing 64 rotates. In addition, the recess 70 prevents migration and lateral movement of the ball bearing 64. In a preferred embodiment, each recess 70 is dimensioned such that a portion of the diameter of the ball bearing 64 resides therewithin. The recess 70 also provides a frictional connection between the housing 18 and the handle 20 of the device 12 to the torque gear 66 and elongated body or shaft 36. It is at this point where the proximal surface 68 of first cavity 22 of the housing 18 meets the ball bearings 64.

In a preferred embodiment, a proximal surface 72 of the torque gear 66 comprises a series of discrete individual divots 74 (FIG. 7) that are positioned radially around a throughbore 76 of the torque gear 66. In a further embodiment, the torque gear 66 comprises an equal number of divots 74 as there are ball bearings 64. It is further preferred that these divots 74 are positioned equidistant from longitudinal axis A-A within the proximal surface 72 of the gear 66.

In addition, each divot 74 is dimensioned such that when the ball bearing 64 is positioned therewithin, the equator of the ball bearing 64 is above the proximal surface 72 of the torque gear 66. In a preferred embodiment, the divot 74 penetrates from about 0.25 cm to about 1.0 cm within the proximal surface 72 of the torque gear 66. Therefore, each of the ball bearings 64 is sandwiched between the divot 74 of the proximal surface 72 of the torque gear 66 and the proximal surface 68 of the first cavity 22 of the housing 18.

In a preferred embodiment, the throughbore 76 of the torque gear 66 comprises a cross-sectional shape that is hexagonal. This preferred hexagonal shape provides a plurality of contact surfaces where the gear 66 and the outer surface 78 of the shaft 36 meet. However, it is contemplated that other non-limiting cross sectional shapes could also be used such that a frictional fit between the shaft 36 and the torque gear 66 is established. As the torque gear 66 is rotated, the contact surfaces where the gear 66 and the outer surface 78 of the shaft 36 meet create a frictional interference with the outer surface of the shaft 36 which, in turn, causes the shaft 36 to rotate with the gear 66. The torque gear 66 preferably comprises a distal surface 80 that is planar and is substantially perpendicular with respect to longitudinal axis A-A.

A thrust bearing 82 is positioned distal of the torque gear 66 (FIG. 8). The thrust bearing 82 comprises a disc 84 with a cylindrical outer diameter. A plurality of balls 86 reside within the thickness of the bearing 82. In a preferred embodiment, the balls 86 are positioned with their equator aligned with the center of the thickness of the disc 84 such that a portion of each of the balls 86 extends past a proximal and distal surface 88, 90 of the thrust bearing 82. Furthermore, it is preferred that a series of eight balls 86 are positioned around the thrust bearing 82. However, the bearing 82 can be designed with more or a less number of balls 86. The thrust bearing 82 preferably comprises an outer diameter ranging from about 1 cm to about 5 cm with an inner diameter ranging from about 1 cm to about 4 cm. It is preferred that a throughbore 92 of the thrust bearing 82 has a cross-sectional shape that is curved and more preferably circular. The thrust bearing 82 resides between a flat washer 94 positioned distal of the bearing 82 and the torque gear 66. Specifically, the balls 86 of the thrust bearing 82 contact the distal surface 80 of the torque gear 66.

A variable force applying subassembly 96 resides distal of the washer 94. The variable force applying subassembly 96 is designed to generate a compressive force that is biased in a proximal direction through the device 12. In a preferred embodiment, the variable force applying subassembly 96 may comprise an adjustment nut 98 and a plurality of Belleville washers 100 arranged front to back in a single stack or multiple stack formation. Alternatively, a spring (not shown) or plurality of springs (not shown) or in combination with the plurality of Belleville washers 100 may also comprise the subassembly 96. The washers 100 and/or springs are further positioned between the flat washer 94 and the adjustment nut 98. Therefore, the plurality of Belleville washers 100 or spring (not shown) provide a compressive force that is transferred through the components of the limiter device 12. In a preferred embodiment, the biasing force generated through compression of the washers 100 and or springs of the variable force applying subassembly 96 compresses the components in a proximal direction against the inner proximal surface 68 of the first cavity 22 within the housing 18. It is this compressive force, generated by the subassembly 96 that correlates to the torque limit of the device 12.

The number and type of Belleville washers 100 and/or springs that comprise the subassembly 96 determine the amount of biasing or compressive force and thus the torque limit of the device 12. Increasing the number of Belleville washers 100 within the subassembly 96 generally increases the amount of the compressive force provided by the subassembly 96. In turn, this increases the amount of torque that is delivered by the device 12. Alternatively, providing a spring (not shown) with an increased torsion moment can also increase the compressive force and the torque amount. Furthermore, multiple stacks of washers 100 can also be provided in combination with the series of Belleville washers 100 and the spring or springs (not shown). The adjustment nut 98, positioned distal of the Belleville washers 100, provides a means by which the washers 100 and/or springs are compressed, thus resulting in the force that is applied by the variable force applying subassembly 96. For example, a torque range from about 5 inch-lbs to about 15 in-lbs can be generated through the use of a series of springs, whereas a torque range from about 25 in-lbs to about 50 in-lbs can be generated through multiple stacking of a plurality of Belleville washers 100.

In a preferred embodiment, the compressive force provided by the variable force applying subassembly 96 compresses against the flat washer 94 which, in turn, compresses against the thrust bearing 82. The thrust bearing 82 thus biases against the plurality of the ball bearings 64 which, in turn, bias against the proximal surface 68 of the first cavity 22. The ball bearings 64 are thus in a biased frictional contact relationship with the housing 18 and the torque gear 66 and shaft 36.

An enclosure 51 may be positioned over the housing 18 within which, comprises the components of the torque limiting mechanism 16. In a preferred embodiment, the enclosure 51 may be in a threaded relationship with the housing 18. Alternatively, the enclosure 51 may be welded or adhered to the housing 18. An enclosure opening 53 is provided at the distal end of the enclosure 51. The opening 53 allows for the passage of the of the shaft 36 therethrough. As shown in FIG. 3, a second retaining ring 55 may be positioned circumferentially around the shaft 36 within the enclosure opening 53. The second retaining ring 55 helps minimize lateral movement of the distal end 40 of the shaft 36 as well as ensure that the shaft 36 remains in a parallel orientation with longitudinal axis A-A.

In operation, torque is applied to the device 12 through rotation of the handle 20, either through manual rotation by the user or through rotation of a connected motor (not shown). Initially, as torque is applied, rotation of the handle 20 rotates the connected housing 18. Rotational movement of the housing 18, in turn, rotates the torque gear 66, which is connected to the housing 18 through the frictional interference contact relationship of the ball bearings 64 and the inner surface of the housing, provided by the variable force applying subassembly 96.

Once the torque applied to the handle 20 through its rotation by an operator exceeds the compressive force applied by the variable force applying subassembly 96, the frictional interference contact between the ball bearings 64 and the housing 18 is overcome. Then the handle 20 and connected housing 18 begin to rotate freely without engaging the torque gear 66 and shaft 36. Therefore, at this point rotation of the handle 20 no longer drives rotation of the elongated body or shaft 36. The applied torque being delivered to the fastener or shaft has therefore been limited.

In addition to the torque limiter device 12, an adapter 14 may be provided with the device assembly 10. The adapter 14, having an adapter distal end portion spaced from an adapter proximal end portion, comprises an adapter elongated body 102, an adapter collar 104, an adapter spring 106, and an o-ring 110 and retaining rings 112A and 112B.

As previously mentioned, the adapter is designed to connect to the distal end portion 40 of the shaft 36 of the torque limiter device 12. In a preferred embodiment, a proximal end portion 114 of the adapter elongated body 102 is connected with the distal end portion 40 of the shaft 36 of the torque limiter device 12. The adapter 14 may be connected to the limiter device 12 through a number of non-limiting means including, welding, soldering, a pin and groove connection or a snap fit mechanism.

The adapter 14 is the conduit between the torque limiter device 12 and a shaft 116 of a secondary device. A secondary device is herein defined as the object with which torque is to be applied. Non-limiting examples of secondary devices comprises a fastener, such as a bolt, screw, nut or a shaft of an auxiliary tool or the like. As such, the distal end of the adapter body 118 may be designed with a variety of cross-sectional shapes including, but not limited to, a rectangle, a square, an oval, a circle, a triangle, or a hexagonal. Furthermore, an adapter body distal end depth 120 may range from about 1 cm to about 10 cm depending on the shape and size of the fastener.

The adapter 14 is primarily comprised of a spring 106 and ball mechanism. This ball and spring mechanism, illustrated in FIGS. 3 and 4, is designed to bias against the outside wall of the fastener thereby securing the fastener therewithin. As illustrated in FIGS. 3 and 4, the adapter elongated body 102 extends parallel to longitudinal axis A-A with an adapter throughbore 125 extending therethrough.

In a preferred embodiment, two opposing balls 122 are positioned about midway between the distal and proximal portions 118, 114 of the adapter elongated body 102. These balls 122 reside within a ball opening 124 that is formed within an adapter body sidewall 126. The ball opening 124 is constructed such that a portion of the ball 122 may extend past the adapter sidewall inner surface 126. In a preferred embodiment, from about 5 percent to about 15 percent of the diameter of the ball 122 extends beyond the adapter body sidewall inner surface 126. It is this portion of the ball 122 that contacts the outer surface of a fastener that has been inserted into the adapter socket 119.

The adapter spring 106 is positioned distal of the balls 122. The spring 106 is further positioned circumferentially around the adapter throughbore 125. In addition, the adapter o-ring 110 is positioned circumferentially around the adapter throughbore 125 and proximal of the spring. This o-ring 110, which is preferably positioned between the adapter spring 106 and a raised outer wall of the adapter throughbore 125, acts as a "back stop" for the spring 106. Residing proximal of the ball 122 is a first adapter retaining ring 112A and a second adapter retaining ring 112B.

The collar 104, having a distal opening spaced apart from a proximal opening, is positioned over these components and serves as an adapter 14 housing. The collar 104 is in a slidable relationship with the throughbore 125. As illustrated in FIGS. 3 and 4, the collar 104 is constructed such that it slides proximally towards the handle 20.

In a preferred embodiment, the collar 104 is designed with a series of inner wall surfaces. A lip 128 resides at the distal end of the collar 104. This lip 128 extends circumferentially around the adapter throughbore 125. A lip end 130 contacts the outer surface of the adapter throughbore wall. Proximal of the lip 128 resides a first adapter inner wall surface 132 that extends circumferentially around the throughbore 125 and longitudinally from the lip end surface. The position of the first adapter inner wall surface 132 and the lip 128 provides a space within which the spring 106 moves. An adapter cavity 134 resides proximal of the first inner wall surface 132. The cavity 134 is positioned circumferentially within the inner wall of the adapter collar 104. The cavity 134 is further dimensioned such that the ball or balls 122 fit therewithin. As the collar 104 is moved in a proximal direction against the spring 106, the cavity 134 is therefore positioned over the ball 122 or balls 122 within the adapter 14.

Positioning the cavity 134 over the balls 122 allows for the balls 122 to move upwardly into the cavity 134 when a fastener and the like is inserted therewithin. As shown in FIGS. 3 and 4, the collar 104 is moved in a proximal direction such that the cavity 134 is slid over the balls 122. The shaft of a fastener or like secondary instrument is then positioned within the throughbore 125 of the adapter 14. As the fastener is inserted therein, the balls 122 are forced to travel upwardly such that a portion of the diameter of the balls 122 extends past an outer surface of the adapter body 14 and into the cavity 134 above. Once the fastener is properly received in the adapter 14, the collar 104 is allowed to move in a distal direction, back to its original starting position. The adapter spring 106 applies a force against the lip of the collar 104 which returns the collar 104 to its original distal position. A second adapter wall surface 136, residing proximal of the cavity 134, is slid over the opening 124 and the ball 122 therewithin. This second adapter wall surface 136 biases a portion of the ball 122 onto the outer surface of the inserted fastener, securing it therewithin. The first and second retaining rings 112A, 112B positioned proximal of the second adapter wall surface provide a means of securing the collar 104 to the adapter body 102.

Once the fastener or like secondary device is secured within the socket 119 of the adapter, the torque limiting device 12 of the present invention is ready for use. The operator may rotate the handle 20 in either a clockwise or counterclockwise direction. As the device 12 is rotated, the handle 20, which is in frictional contact with the ball bearings, rotates the elongated body or shaft 36 of the device 12. The elongated body 36 in turn, rotates the adapter 14 at its distal end which then rotates the fastener therewithin.

The force applied by the compressed Belleville washers 100 or spring (not shown) within the housing 18 of the handle 20 of the device biases the ball bearings 64 within the thrust bearing 82. These thrust bearing balls 86 in turn apply a biasing force against the distal surface of the torque gear 66 in a proximal direction. The biasing force is then transferred to the ball bearings 64 which, in turn, bias against the proximal surface of the first cavity wall 68 within the housing 18. These series of biasing forces from the Belleville washer 100 at the distal end of the device 12 to the proximal wall surface 68 of the housing 18 provide a frictional interference connection between the torque gear 66 and the handle 20. Once a specified torque value has been exceeded by rotation of the handle 20, the force of the torque applied to the handle 20 exceeds the force applied by the Belleville washers 100. At this point, the frictional connection between the ball bearings 64 and the handle 20 is overcome and the handle 20 begins to rotate about the longitudinal axis A-A without turning the torque gear 64. The locking bushing 52 positioned proximally adjacent the ball bearings 64 applies a distal force counter to the proximal force applied by the Belleville washers 100. This counter force provides additional alignment of the ball bearings 64 and ensures translational movement of the shaft 36 of the device 12 is minimized. Additionally, the locking bushing 52 ensures that the ball bearings 64 prevent side movement of the bearings 64, thus ensuring correct alignment between the bearings 64 and the housing 18.

Furthermore, the retaining ring 60 positioned proximal of the locking bushing prevents translational movement of the elongated body 36 or shaft of the device 12. Therefore, the retaining ring 60 ensures that the elongated body 36 within the device 12 remains parallel to the longitudinal A-A axis, thereby preventing the type of binding that is prone to the prior art devices.

The attached drawings represent, by way of example, different embodiments of the subject of the invention. Multiple variations and modifications are possible in the embodiments the invention described here. Although certain illustrative embodiments of the invention have been shown and described here, a wide range of modifications, changes, and substitutions is contemplated in the foregoing disclosure. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A torque limiting device comprising:
   a) a housing comprising a housing sidewall extending along a longitudinal axis from a proximal housing portion to a distal housing portion having an annular housing edge spaced from the axis to provide an open distal end, wherein the proximal housing end supports a handle and wherein an internal housing recess provided by the housing sidewall extends from the open distal housing end to the proximal housing portion;
   b) a first shaft partially housed inside the housing and extending from a proximal shaft portion to a distal shaft portion having a distal socket opening, wherein the proximal shaft portion is supported by the proximal housing portion with the distal shaft portion extending axially beyond the open distal housing end;
   c) a lock bushing supported on the first shaft and seated against an inner surface of the housing sidewall, wherein the lock bushing has a distal bushing face that angles distally and inwardly toward the longitudinal axis;
   d) a torque gear friction fit on the first shaft and having a distal torque gear face spaced from a proximal torque gear face, wherein the proximal torque gear face has at least two divots recessed therein;
   e) at least two first ball bearings residing in the respective torque gear divots, wherein the two first ball bearings contact the angled distal bushing face and are seated in bearing recesses formed in the internal surface of the housing sidewall;
   f) a thrust bearing supported op the first shaft and comprising a disc thickness extending to opposed proximal and distal disc faces, wherein the thrust bearing comprises at least two second ball bearing supported by the disc with the second ball bearings being of a greater diameter than that of the disc thickness so that the second ball bearings contact the proximally positioned torque gear and extend beyond the distal disc face;
   g) a first spring supported on the first shaft;
   h) a nut threaded into engagement with the inner surface of the housing sidewall at the distal housing portion, wherein the nut forces the first spring into biased relationship against the second ball bearings of the thrust bearing and in turn the torque gear including the first ball bearing seated in the bearing recesses of the housing sidewall and contacting the angled distal bushing face; and
   i) an enclosure comprising an enclosure sidewall extending from a distal enclosure portion an having an open distal enclosure end to a proximal enclosure portion providing an open proximal housing end, wherein the proximal enclosure portion is mated to the distal housing portion with the distal first shaft portion including the distal socket opening extending axially beyond the open distal enclosure end;
   j) wherein the nut is threadingly adjustable to adjust the bias of the first spring against the thrust gear and the torque gear including the first ball bearings;
   k) wherein rotation of the handle causes rotation of the torque gear and the friction fit first shaft inside the housing until a maximum threshold torque force provided by the adjustable bias of the first spring is exceeded, and
   l) wherein when the maximum threshold torque force is exceeded, the first shaft and torque gear cease to rotate in unison with the handle as the torque gear rotates on the first ball bearings seated in the bearing recesses of the housing sidewall and contacting the angled distal bushing face.

2. The torque limiting device of claim 1, wherein the internal housing recess comprises a first cavity, a second cavity and a third cavity therewithin, wherein the second cavity is proximal the first cavity and the third cavity is proximal the second cavity.

3. The torque limiting device of claim 2, wherein the proximal first shaft portion is supported within the third cavity of the internal housing recess.

4. The torque limiting device of claim 2, wherein a first retaining ring resides circumferentially around the first shaft, proximal the lock bushing and distal the first ball bearings.

5. The torque limiting device of claim 4, wherein the lock bushing and the first retaining ring reside in the second cavity of the housing.

6. The torque limiting device of claim 4, wherein the internal housing recess comprises a first cavity, a second cavity and a third cavity, therewithin, the second cavity being proximal the first cavity and the third cavity being proximal the second cavity and wherein the first retaining ring resides in the second cavity of the housing recess.

7. The torque limiting device of claim 2, wherein the bearing recesses are formed within the second cavity of the internal surface of the housing.

8. The torque limiting device of claim 1, wherein the torque gear comprises a plurality of first ball bearings recessed in respective divots in the proximal torque gear face, the plurality of first ball bearings being positioned circumferentially around the first shaft.

9. The torque limiting device of claim 1, wherein the proximal torque gear face has a plurality of divots recessed therein.

10. The torque limiting device of claim 9 wherein the plurality of first ball bearings of the torque gear reside at regularly spaced intervals circumferentially around the shaft.

11. The torque limiting device of claim 1, wherein the distal bushing face is angled from about 35° to about 50° with respect to the longitudinal axis.

12. The torque limiting device of claim 1, wherein the first spring supported on the first shaft comprises a plurality of Belleville washers.

13. The torque limiting device of claim 1 further comprising an adapter connected to the distal shaft portion, the adapter comprising:
  a) an adapter shaft having an adapter shaft sidewall extending from a distal adapter shaft portion, an adapter throughbore extending therebetween, wherein the proximal adapter shaft portion is received in the socket opening of the first shaft;
  b) at least one third ball positioned within an opening of the adapter shaft sidewall;
  c) a collar positioned circumferentially over the distal adapter shaft portion;
  d) a second spring positioned circumferentially over the adapter shaft; and
  e) wherein the collar is manipulatable in a proximal direction to position a first inner adapter wall surface providing a cavity in radial alignment with the third ball so that the third ball is movable into the cavity when a tool shaft is moved into the adapter shaft throughbore, and
  f) wherein the collar is movable in a distal direction by the bias of the second spring to move a second inner adapter wall surface into radial alignment with the third ball to thereby block the third ball partially extending into the adapter shaft throughbore to thereby prevent the tool shaft from being moved out of the adapter shaft throughbore.

14. The torque limiting device of claim 1 wherein the second ball hearings of the thrust bearing are substantially centered in the disc thickness of the disc.

15. A torque limiting devices comprising:
  a) a housing comprising a housing sidewall extending along a longitudinal axis from a proximal housing portion to a distal housing portion having an annular housing edge spaced from the axis to provide an open distal housing end, wherein the proximal housing end supports a handle and wherein an internal housing recess provided by the housing sidewall extends from the open distal housing end to the proximal housing portion;
  b) a shaft partially housed inside the housing and extending from a proximal shaft portion to a distal shaft portion having a distal socket opening, wherein the proximal shaft portion is supported by the proximal housing portion with the distal shaft portion extending axially beyond the open distal housing end;
  c) a lock bushing supported on the shaft and seated against an inner surface of the housing sidewall, wherein the lock bushing has a distal bushing face that angles distally and inwardly toward the longitudinal axis;
  d) a torque gear friction fit on the shaft and having a distal torque gear face spaced from a proximal torque gear face, wherein the proximal torque gear face has at least two divots recessed therein;
  e) at least two first ball bearings residing in the respective torque gear divots, wherein the two first ball bearings contact the angled distal bushing face and are seated in bearing recesses formed in the internal surface of the housing sidewall;
  f) a thrust bearing supported on the shaft and comprising a disc having a disc thickness extending to opposed proximal and distal disc faces, wherein the thrust bearing comprises at least two second ball bearings supported by the disc with the second ball bearings being of a greater diameter than that of the disc thickness so that the second ball bearings contact the proximally positioned torque gear and extend beyond the distal disc face;
  g) a spring supported on the shaft;
  h) a nut threaded into engagement with the inner surface of the housing sidewall at the distal housing portion, wherein the nut forces the spring into a biased relationship against the second ball bearings of the thrust bearing and in turn the torque gear including the first ball bearings seated in the bearing recesses of the housing sidewall and contacting the angled distal bushing face; and
  i) an enclosure comprising an enclosure sidewall extending from a distal enclosure portion having an open distal enclosure end to a proximal enclosure portion providing an open proximal housing end, wherein the proximal enclosure portion is threadingly mated to the distal housing portion with the distal shaft portion including the distal socket opening extending axially beyond the open distal enclosure end;
  j) wherein the nut is threadingly adjustable to adjust the bias of the spring against the thrust gear and the torque gear including the first ball bearings;
  k) wherein rotation of the handle causes rotation of the torque gear and the friction fit shaft inside the housing until a maximum threshold torque force provided by the adjustable bias of the spring is exceeded, and
  l) wherein when the maximum threshold torque force is exceeded, the shaft and torque gear cease to rotate in unison with the handle as the torque gear rotates on the first ball bearings seated in the bearing recesses of the housing sidewall and contacting the angled distal bushing face, and
  m) wherein the proximal enclosure portion is unthreadable from the distal housing portion to adjust the threaded engagement of the nut with the inner surface of the housing sidewall at the distal housing portion to thereby adjust the bias of the spring.

16. The torque limiting device of claim 15 wherein a first retaining ring resides circumferentially around the shaft, proximal the lock bushing and distal the first ball bearings.

17. The torque limiting device of claim 16 wherein the internal housing recess comprises a first cavity, a second cavity and a third cavity therewithin, the second cavity being proximal the first cavity and the third cavity being proximal the second cavity and wherein the first retaining ring resides in the second cavity of the housing.

18. The torque limiting device of claim 15 wherein the torque gear comprises a plurality of first ball bearings recessed in respective divots in the proximal torque gear face, the plurality of first ball bearings being positioned circumferentially around the shaft.

19. The torque limiting device of claim 15 wherein the distal bushing face is angled from about 35° to about 50° with respect to the longitudinal axis.

20. The torque limiting device of claim 15 wherein the first spring supported on the shaft comprises a plurality of Belleville washers.

21. The torque limiting device of claim 15 wherein the second ball bearings of the thrust bearing are substantially centered in the disc thickness of the disc.

22. The torque limiting device of claim 15 wherein the proximal torque gear face has a plurality of divots recessed therein.

23. The torque limiting device of claim 22 wherein the plurality of first ball bearings of the torque gear reside at regularly spaced intervals circumferentially around the shafts.

* * * * *

UNITED STATES PATENT AND TRADEMARK OFFICE
CERTIFICATE OF CORRECTION

PATENT NO. : 8,714,056 B2
APPLICATION NO. : 13/224659
DATED : May 6, 2014
INVENTOR(S) : Steve Landowski It is certified that error appears in the above-identified patent and that said Letters Patent is hereby corrected as shown below:

In the Claims

Column 10, line 14 (Claim 1, line 27) delete "formed in" and insert --of--

Column 10, line 16 (Claim 1, line 29) delete "op" and insert --on--

Column 10, line 17 (Claim 1, line 30) after the word "comprising" insert --a disc having--

Column 10, line 19 (Claim 1, line 32) delete "bearing" and insert --bearings--

Column 10, line 27 (Claim 1, line 40) after the word "into" insert --a--

Column 10, line 34 (Claim 1, line 47) after the word "portion" delete "an"

Column 10, line 54 (Claim 2, line 1) after the word "claim 1" delete the ","

Column 10, line 59 (Claim 3, line 1) after the word "claim 2" delete the ","

Column 10, line 62 (Claim 4, line 1) after the word "claim 2" delete the ","

Column 10, line 65 (Claim 5, line 1) after the word "claim 4" delete the ","

Column 11, line 3 (Claim 6, line 3) after the word "cavity" delete the ","

Column 11, line 7 (Claim 7, line 1) after the word "claim 2" delete the ","

Column 11, line 10 (Claim 8, line 1) after the word "claim 1" delete the ","

Column 11, line 15 (Claim 9, line 1) after the word "claim 1" delete the ","

Signed and Sealed this
Sixth Day of January, 2015

Michelle K. Lee
*Deputy Director of the United States Patent and Trademark Office*

CERTIFICATE OF CORRECTION (continued)
U.S. Pat. No. 8,714,056 B2

Column 11, line 20 (Claim 11, line 1) after the word "claim 1" delete the ","

Column 11, line 23 (Claim 12, line 1) after the word "claim 1" delete the ","

Column 11, line 30 (Claim 13, line 5) after the word "from" insert --a proximal adapter shaft portion spaced from--

Column 12, line 14 (Claim 15, line 30) delete "formed in" and insert --of--